United States Patent
Li et al.

(10) Patent No.: US 11,523,985 B2
(45) Date of Patent: Dec. 13, 2022

(54) FORMULATIONS, METHODS, AND SYSTEMS FOR TREATING GENITOURINARY CONDITIONS

(71) Applicants: Massachusetts Institute of Technology, Cambridge, MA (US); The General Hospital Corporation, Boston, MA (US)

(72) Inventors: Xiang Li, Brookline, MA (US); Michael J. Cima, Winchester, MA (US); Brian H. Eisner, Needham, MA (US)

(73) Assignees: Massachusetts Institute of Technology, Cambridge, MA (US); The General Hospital Corporation, Boston, MA (US)

( * ) Notice: Subject to any disclaimer, the term of this patent is extended or adjusted under 35 U.S.C. 154(b) by 320 days.

(21) Appl. No.: 16/605,092

(22) PCT Filed: Apr. 13, 2018

(86) PCT No.: PCT/US2018/027474
§ 371 (c)(1),
(2) Date: Oct. 14, 2019

(87) PCT Pub. No.: WO2018/191607
PCT Pub. Date: Oct. 18, 2018

(65) Prior Publication Data
US 2020/0405631 A1    Dec. 31, 2020

Related U.S. Application Data

(60) Provisional application No. 62/485,594, filed on Apr. 14, 2017.

(51) Int. Cl.
*A61K 31/4409* (2006.01)
*A61K 9/00* (2006.01)
(Continued)

(52) U.S. Cl.
CPC .......... *A61K 9/0034* (2013.01); *A61K 9/0002* (2013.01); *A61K 31/4409* (2013.01); *A61K 31/4422* (2013.01); *A61K 45/06* (2013.01)

(58) Field of Classification Search
CPC ................................................. A61K 31/4409
See application file for complete search history.

(56) References Cited

U.S. PATENT DOCUMENTS

| | | | |
|---|---|---|---|
| 2006/0058355 A1* | 3/2006 | Dittrich | A61K 31/4164 514/338 |
| 2007/0248639 A1 | 10/2007 | Demopulos et al. | |
| 2008/0234659 A1 | 9/2008 | Cheng et al. | |

FOREIGN PATENT DOCUMENTS

| | | |
|---|---|---|
| EP | 2351569 A1 | 8/2011 |
| WO | 2009/079011 A1 | 6/2009 |

OTHER PUBLICATIONS

Extended European Search Report for EP 18784006.1, dated Mar. 17, 2021 (9 pages).

(Continued)

*Primary Examiner* — Benjamin J Packard
(74) *Attorney, Agent, or Firm* — Eversheds Sutherland (US) LLP

(57) ABSTRACT

Provided are formulations and methods for treating one or more genitourinary conditions. The formulations may include a therapeutic agent that includes a calcium channel blocker, a rho kinase inhibitor, or a combination thereof. The methods may include locally administering a therapeutic agent into a ureter. Systems for delivering a therapeutic agent also are provided.

22 Claims, 7 Drawing Sheets

(51) Int. Cl.
*A61K 31/4422* (2006.01)
*A61K 45/06* (2006.01)

(56) References Cited

OTHER PUBLICATIONS

Levent et al., "Expression of Rho-kinase (ROCK-1 and ROCK-2) and its substantial role in the contractile activity of the sheep ureter," British Journal of Pharmacology, 2004, vol. 143, pp. 431-437.
Nagatoya et al., "Y-27632 prevents tubulointerstitial fibrosis in mouse kidneys with unilateral ureteral obstruction," Kidney International, 2002, vol. 61, pp. 1684-1695.
PCT International Search Report and Written Opinion for PCT Application No. PCT/US2018/027474 dated Sep. 4, 2018 (12 pages).
Liu et al., "Regulation of Rho/ROCK Signaling in Airway Smooth Muscle by Membrane Potential and [CA2+]i," Am J Physiol Lung Cell Mol Physiol, 2005, 289:L574-L582.

* cited by examiner

FORMULATIONS, METHODS, AND SYSTEMS FOR TREATING GENITOURINARY CONDITIONS

CROSS-REFERENCE TO RELATED APPLICATIONS

This application claims priority to U.S. Provisional Patent Application No. 62/485,594, filed Apr. 14, 2017, which is incorporated herein by reference.

BACKGROUND

Urinary stone disease is a common cause of morbidity. According to a recent study, 12% of men and 5% of women by age 70 will have at least one symptomatic urinary stone. Kidney stones may become lodged in the ureter, which may result in one or more of extreme pain, nausea, vomiting, emergency department visits, missed work, and, for some patients, surgical procedures to remove stones that fail to pass.

Various classes of drugs have been contemplated for oral dosing to aid urinary stone passage. According to studies, these oral medications are often ineffective as the oral dose is insufficient for eliciting the desired physiological effect of ureteral relaxation. Amplification of ureteral relaxation through increased oral dosing is impractical, unsafe, or both. This is usually because these drugs have lethal systemic side effects at increased oral dosages. For example, conventional oral medications, such as α-blockers or calcium channel blockers, cannot be increased arbitrarily as oral α- and calcium channel blockers affect muscle function and regulate systemic conditions, such as blood pressure and/or cardiac function. Significant systemic risks, therefore, limit the dosage any patient can receive.

Nevertheless, first line therapy for patients having urinary stones typically includes oral fluid and pain management, in order to manage a patient's pain level and provide hydration to "flush" the stone through the urinary tract spontaneously. Spontaneous stone passage, however, is largely determined by stone size. Stones 2-4 mm in diameter have a 95% chance of passage, but stones >5 mm require surgical intervention nearly 50% of the time (Macario, A. et al., *Anesth. Analg.*, vol. 89, no. 5, pp. 1241-1245, November 1999). An average of 1-3 weeks is required for spontaneous passage (~8.2 days for stones <2 mm, 12.2 days for stones 2-4 mm, 22.1 days for stones 4 mm or greater). These durations can decrease the patients' quality of life, and increase the reliance on oral-pain medications, including opioid medications.

Although the oral management of urinary stones typically includes the off-label use of α-blockers or calcium channel blockers, there remains no FDA-approved therapeutic directly indicated for expediting passage of urinary stones (Hollingsworth, J. M. et al., *Lancet*, vol. 368, no. 9542, pp. 1171-1179, September 2006). Providers routinely prescribe tamsulosin hydrochloride (FLOMAX, an α-blocker used for difficulty urinating due to benign prostate hyperplasia) or calcium channel blockers indicated for hypertension (Perumal, C. et al. *Urol. Ann.*, vol. 7, no. 1, pp. 74-78, March 2015).

These drugs are used because when a stone obstructs the ureter, the typical, natural response for the human ureter is to undergo peristaltic contractions, an involuntary physiological response in an effort to rid the obstruction (Biancani, P. et al. *Am. J. Physiol.*, vol. 231, no. 2, pp. 393-398, August 1976). Continued ureteral contractions around the stone, however, can lead to pain, local inflammation, and/or swelling that can become prohibitive to stone passage (Rule, A. D. et al., *J. Am. Soc. Nephrol. JASN*, vol. 25, no. 12, pp. 2878-2886, December 2014). Off-label medications continue to be used, however, even though a recent 2015 study, which provided patients an α-blocker, a calcium channel blocker, or placebo, revealed no clinical difference in time to passage among the different therapies (Pickard, R. et al., *The Lancet*, vol. 386, no. 9991, pp. 341-349, July 2015). The results of this trial reflected typical clinical outcomes, as only 20-50% of all urinary stone patients on oral medications spontaneously pass their kidney stones (Küpeli, B. et al., *Urology*, vol. 64, no. 6, pp. 1111-1115, December 2004). Failure to pass a stone can result in additional intervention (usually surgical lithotripsy), which can further contribute to the cost of stone disease.

For expedited urinary stone passage, the implementation of a stent (WO2008115543) in a ureter has been reported, as well as a formulation of local diazepam only (US20100272806). Diazepam, however, can be dangerous, even at low doses, and can involve significant risk factors (see, e.g., Lader, M. *J. Clin. Psychiatry*, vol. 48 Suppl, pp. 12-16, December 1987; and Canda, A. E., et al. *Urol. Int.*, vol. 78, no. 4, pp. 289-298, 2007). Furthermore, the ureters lack discrete neuromuscular junctions (which is the primary mode of action for Diazepam), and there is no known mechanism of action for diazepam and no clinical evidence that it works (Wein, A. J. et al. *Campbell-Walsh Urology*, 9th ed., vol. 2, 4 vols; and Burnstock, G. et al. *Circ. Res.*, vol. 27, p. Suppl 2:5-23, October 1970).

There remains a need for improved treatments of urinary stones, especially in view of the fact that there are no existing FDA-approved products indicated for expedited stone passage (outside of lithotripsy and off-label oral medication use), and a significant proportion of patients that have urinary stones do not pass them spontaneously and require surgical intervention. There also remains a need for treatments of ureters via a local delivery approach that may achieve a relaxation of the ureter. Increasing relaxation of the ureter may expedite time to passage of a urinary stone, which may reduce pain, improve quality of life, and/or diminish a patient's reliance on pain medications, such as opioids. The relaxation of the ureter also may be used in the treatment of other genitourinary conditions where triggering the physiology of smooth muscle to facilitate relaxation provides a positive clinical outcome. Also, facilitating a significant and targeted relaxation effect typically requires micromolar concentrations or higher dosing in the ureter, which is not possible to achieve safely via oral dosing.

Other objects, features, and advantages of the invention will be apparent from the following detailed description, drawings, and claims. Unless otherwise defined, all technical and scientific terms and abbreviations used herein have the same meaning as commonly understood by one of ordinary skill in the art to which this invention pertains. Although methods and formulations similar or equivalent to those described herein can be used in the practice of the present invention, suitable methods and formulations are described without intending that any such methods and formulations limit the invention herein.

BRIEF SUMMARY

Provided herein are formulations, systems, and methods for local delivery of therapeutic agents to a ureter to provide therapy for genitourinary conditions, relax ureteral smooth muscle, or a combination thereof. The therapeutic agents, for example, may relax ureteral smooth muscle, thereby providing therapy for urinary stones. The therapeutic agents may include two or more components that exhibit a synergistic effect on the relaxation of ureteral smooth muscle. The methods and formulations herein may deliver doses to a ureter that significantly exceed (e.g., by up to 100,000×) the doses available through systemic oral dosing, while potentially circumventing one or more systemic side effects.

In one aspect, methods are provided for treating a patient having a genitourinary condition. In embodiments, the methods include locally administering into a ureter of a patient a formulation that includes a therapeutically effective amount of a therapeutic agent selected from a calcium channel blocker, a rho kinase inhibitor, or a combination thereof. In some embodiments, the therapeutic agent includes the calcium channel blocker and the rho kinase inhibitor.

In another aspect, methods are provided for relaxing ureteral smooth muscle in vivo. In embodiments, the methods include locally administering into a ureter of a patient a formulation that includes a therapeutically effective amount of a combination of a calcium channel blocker and a rho kinase inhibitor. In further embodiments, the methods include locally administering into a ureter of a patient a formulation that includes a therapeutically effective amount of a therapeutic agent selected from a calcium channel blocker, a rho kinase inhibitor, or a combination thereof. In still further embodiments, the methods include locally administering into a ureter of a patient a therapeutic agent to exhibit a relaxing effect on human ureteral smooth muscle of at least 20% when administered at a dose and concentration suitable for the locally administering, wherein the therapeutic agent includes an alpha-adrenergic receptor agonist, a phosphodiesterase type 5 inhibitor, or a combination thereof.

In yet another aspect, formulations for local administration to a ureter of a patient are provided. In embodiments, the formulations include a therapeutic agent selected from a calcium channel blocker, a rho kinase inhibitor, or a combination thereof; and one or more pharmaceutically acceptable excipients, wherein the formulation is suitable for local administration into the ureter.

In a further aspect, drug delivery systems are provided. In embodiments, the drug delivery systems include a delivery device having at least a part thereof which is configured for insertion into a ureter of a patient; and a formulation including a therapeutic agent selected from a calcium channel blocker, a rho kinase inhibitor, or a combination thereof, wherein the delivery device is configured to deliver the therapeutic agent to the ureter in an amount effective to relax ureteral smooth muscle in vivo.

DETAILED DESCRIPTION

Figure 1:
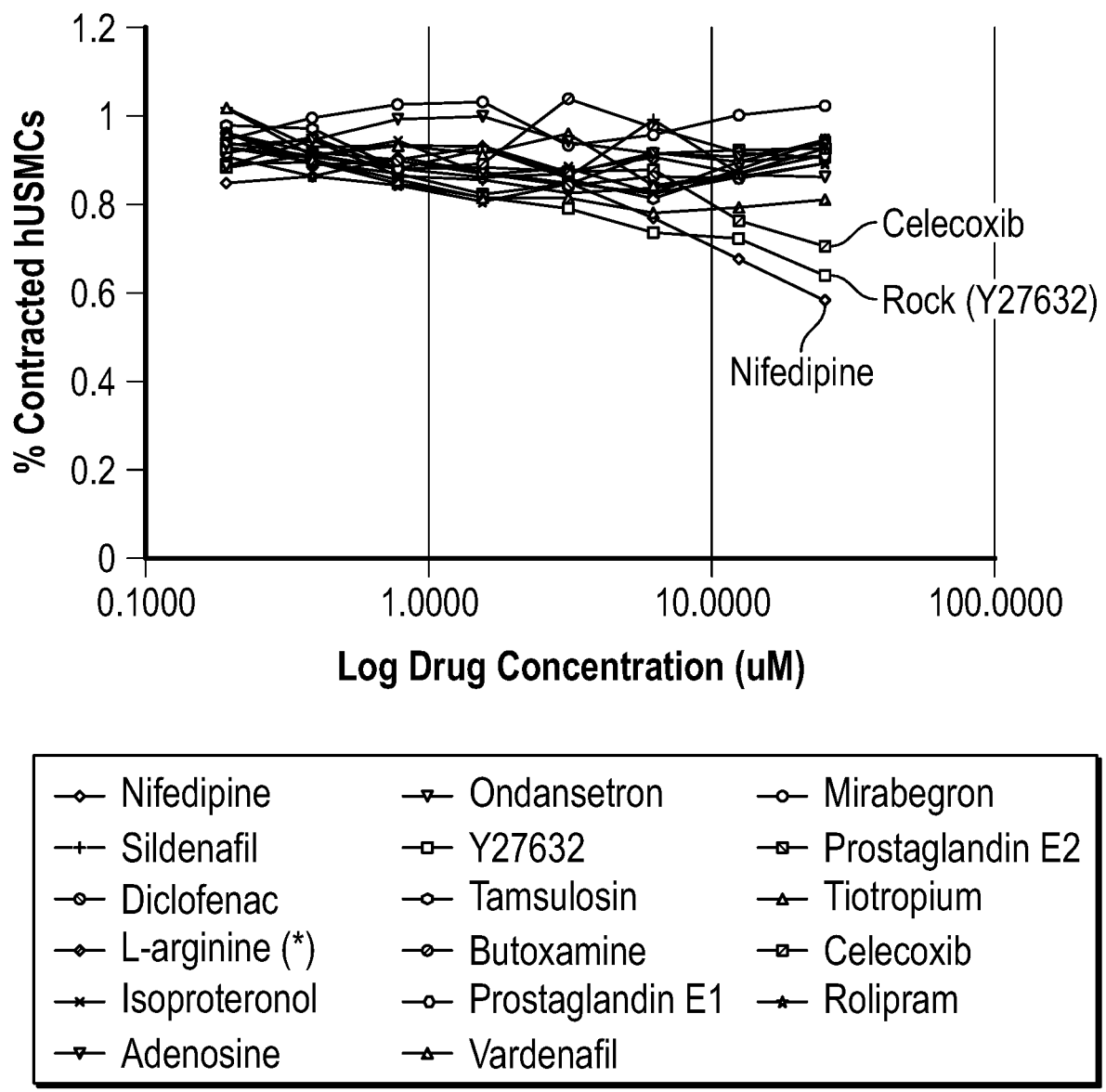
FIG. 1 depicts the effect of a series of therapeutic agents on smooth muscle relaxation, according to the test of Example 1.

Provided herein are formulations for local administration to a ureter of a patient. The formulations include a therapeutic agent. In some embodiments, the formulations include a therapeutic agent and a pharmaceutically acceptable excipient. Applicant has discovered that certain therapeutic agents are particularly advantageous for use in relaxing the smooth muscle of ureters, and that certain combinations of therapeutic agents are particularly beneficial in this regard.

The formulations provided herein may be suitable for local administration into a ureter. The formulations provided herein generally may be in any form that permits local administration to a ureter. In some embodiments, the formulations are in the form of a gel, such as a hydrogel, or other viscous vehicle, such as a lubricant. In some embodiments, the formulations are in the form of an aqueous liquid solution. In some embodiments, the formulations are part of a ureteral stent or other medical device that is insertable and/or implantable into a patient. The formulations, for example, may be provided as a continuous or discontinuous coating of a ureteral stent or other medical device. In some embodiments, the formulations may be in the form of a lubricant, and may include commercially available lubricants used with surgical instruments, gloves, catheters, etc.

The formulations may have one or more features for controllably releasing a therapeutic agent, delaying or preventing passage of a formulation from a ureter, or a combination thereof. For example, the formulation may include a hydrogel and/or lubricant having a viscosity that delays or prevents passage of the formulation from a ureter. The hydrogel and/or lubricant also or alternatively may serve as a matrix from which a therapeutic agent is controllably released.

The term "hydrogel" refers to a material formed from a cross-linked network of polymer chains. A variety of hydrogels can be developed by manipulating the polymer formulation and the cross linking mechanism. Crosslinks can be formed through both chemical and physical means. The result is a hydrophilic material with unique mechanical and physical properties, including the ability to imbibe water and swell. Many hydrogels have been developed that are environmentally sensitive to factors such as pH, temperature, and ionic strength. Hydrogels are frequently used in bioengineering because they are easily modified and highly biocompatible. In some embodiments, the formulation is a hydrogel, and the hydrogel includes polyethylene glycol (PEG). PEG is a synthetic polyether that is biologically compatible due to its low toxicity and hydrophillicity. It is frequently used in vivo because it does not activate an immune response and prevents protein adhesion to surfaces. PEG chains can be easily functionalized with terminal acrylate groups to form PEG-diacrylate or PEG-dimethacrylate for crosslinking purposes.

The term "lubricant" refers to a substance that reduces friction between two or more contacting surfaces, and may include water-based, oil-based, and/or silicone-based materials. The lubricants herein may include sterile gels, including, for example, sterile hydrogels, and may contain a bacteriostatic agent. The lubricants herein may include petroleum jelly, hydroxyethyl cellulose, hypromellose, propylene glycol, water, or a combination thereof. One or more properties of the lubricants herein, such as viscosity, may be modified by altering a ratio of the components. The lubricants herein, in some embodiments, can deliver a therapeutic agent at concentrations up to 1000 μM.

A formulation may be locally administered directly to a ureter without a delivery device, or a formulation may be locally administered to a ureter via a delivery device.

When the formulations include a therapeutic agent and a pharmaceutically acceptable excipient, the formulations may include a therapeutically effective amount of the therapeutic agent, and the weight ratio of the therapeutic agent to the pharmaceutically acceptable excipient generally may include any weight ratio that does not undesirably impact the therapeutic effect of the therapeutic agent. In some embodiments, the weight ratio of the therapeutic agent to the pharmaceutically acceptable excipient is about 1:0.1 to about 1:100, about 1:0.5 to about 1:75, about 1:0.5 to about 1:50, about 1:05 to about 1:25, about 1:0.5 to about 1:10, or about 1:1 to about 1:10.

A therapeutic agent and a pharmaceutically acceptable excipient may be associated with each other in any manner. For example, a therapeutic agent may be substantially uniformly dispersed in a pharmaceutically acceptable excipient. As a further example, a therapeutic agent may be disposed in one or more voids defined by a pharmaceutically acceptable excipient.

Therapeutic Agents

The therapeutic agents provided herein may include one or more components capable of relaxing ureteral smooth muscle. The therapeutic agents may include a component from one or more of the following classes of components: α-adrenoceptor agonists, β-adrenoceptor agonists, phosphodiesterase (PDE) inhibitors, calcium channel blockers, rho-kinase inhibitors, prostaglandins (PG) & cyclooxygenase (COX), seratonin (5-HT), or nitric oxide (NO) donors.

Non-limiting examples of α-adrenoceptor agonists include tamsulosin (HCl). Non-limiting examples of β-adrenoceptor agonists include isoproterenol, butoxamine (HCl), and mirabegron. Non-limiting examples of phosphodiesterase (PDE) inhibitors include sildenafil, vardenafil, and rolipram. Non-limiting examples of calcium channel blockers include nifedipine, cilnidipine, amilodipine, and nitrendipine. Non-limiting examples of rho-kinase inhibitors include Y-27632 (HCl), fasudil, and ripasudil. Non-limiting examples of prostaglandins include prostaglandin E1 and prostaglandin E2. Non-limiting examples of nonsteroidal anti-inflammatory drugs (NSAIDs) include diclofenac (sodium) and celecoxib. Non-limiting examples of seratonins (5-HT) include ondansetron (HCl). Non-limiting examples of nitric oxide (NO) donors include L-arginine. Other possible components of the therapeutic agents provided herein include tiotropium and adenosine, which may be used alone, in combination with each other, or in combination with any components of the foregoing classes.

In some embodiments, the therapeutic agent is selected from a calcium channel blocker, a rho kinase inhibitor, or a combination thereof.

In some embodiments, the therapeutic agent includes a calcium channel blocker, and a rho kinase inhibitor, wherein the calcium channel blocker is nifedipine, and the rho kinase inhibitor is Y-27632.

In some embodiments, the therapeutic agent includes a calcium channel blocker and a rho kinase inhibitor, wherein the calcium channel blocker is nifedipine.

In some embodiments, the therapeutic agent includes a calcium channel blocker and a rho kinase inhibitor, wherein the rho kinase inhibitor is Y-27632.

In some embodiments, the therapeutic agent includes a calcium channel blocker and a rho kinase inhibitor, wherein the calcium channel blocker is nifedipine, and the rho kinase inhibitor is Y-27632.

In some embodiments, the therapeutic agent include an alpha-adrenergic receptor agonist, a phosphodiesterase type 5 inhibitor, or a combination thereof. In some embodiments, the therapeutic agent includes the alpha-adrenergic receptor agonist, and the alpha-adrenergic receptor agonist is tamsulosin. In some embodiments, the therapeutic agent includes the phosphodiesterase type 5 inhibitor, and the phosphodiesterase type 5 inhibitor is vardenafil. In some embodiments, the therapeutic agent includes the alpha-adrenergic receptor agonist and the phosphodiesterase type 5 inhibitor, and the alpha-adrenergic receptor agonist is tamsulosin, and the phosphodiesterase type 5 inhibitor is vardenafil.

Pharmaceutically Acceptable Excipients

Pharmaceutically acceptable excipients are known in the art and may include viscosity modifiers, bulking agents, surface active agents, dispersants, osmotic agents, diluents, and other non-active ingredients of the formulation intended to facilitate handling, stability, dispersibility, wettability, and/or release kinetics of a therapeutic agent (i.e., the active pharmaceutical ingredient). A surface active agent may be used to increase the solubility of a therapeutic agent. When, for example, a therapeutic agent is combined with a water-based hydrogel and/or water-based lubricant, a surface active agent may increase the solubility of a therapeutic agent in the water-based hydrogel and/or water-based lubricant.

The excipient of a formulation may be a matrix material, selected to modulate or control the rate of release of the therapeutic agent. The matrix material may be a resorbable or non-resorbable polymer. The matrix material may be a hydrogel and/or lubricant. An excipient may include a hydrophobic or amphiphilic compound, such as a lipid (e.g., selected from fatty acids and derivatives, mono-, di- and triglycerides, phospholipids, sphingolipids, cholesterol and steroid derivatives, oils, vitamins and terpenes).

The combination of the therapeutic agent and the pharmaceutically acceptable excipient may take a variety of suitable forms. For example, it may be a solution, a suspension, a liquid, a gel, or a lubricant. The therapeutic agent may be in a micro particulate form, for example, that is dispersed in a gel, lubricant, or liquid excipient vehicle.

Methods

Provided herein are methods for treating a patient having a genitourinary condition, relaxing ureteral smooth muscle, or a combination thereof. The term "patient" generally refers to a human, although other mammals may be considered a patient in some applications. Non-limiting examples of genitourinary conditions include a urinary stone lodged within the lumen of a ureter, pain from ureteral stent, a genitourinary obstruction, benign prostatic hyperplasia, difficulty voiding, or a combination thereof. The methods of relaxing ureteral smooth muscle provided herein may be used where relaxation of a patient's genitourinary tract is desirable, such as during a surgical operation. For example, a formulation may be locally administered into a ureter prior to a surgical operation to facilitate passage of tools, devices, or objects through the genitourinary tract of a patient.

In embodiments, the methods for treating a patient having a genitourinary condition include locally administering into a ureter of the patient a formulation that includes a therapeutically effective amount of a therapeutic agent.

In embodiments, the methods for relaxing human ureteral smooth muscle in vivo may include locally administering into a ureter of a patient a formulation that includes a therapeutically effective amount of a combination of a calcium channel blocker and a rho kinase inhibitor. In some embodiments, methods for relaxing human ureteral smooth muscle in vivo include locally administering into a ureter of a patient a formulation that includes a therapeutically effective amount of a therapeutic agent selected from a calcium channel blocker, a rho kinase inhibitor, or a combination thereof. The calcium channel blocker may be nifedipine, and the rho kinase inhibitor may be Y-27632.

In embodiments, the methods for relaxing human ureteral smooth muscle in vivo include locally administering into a ureter of a patient a therapeutic agent to exhibit a relaxing effect on human ureteral smooth muscle of at least 20% when administered at a dose and concentration suitable for the locally administering. The therapeutic agent may include an alpha-adrenergic receptor agonist, a phosphodiesterase type 5 inhibitor, or a combination thereof. In some embodiments, the therapeutic agent includes the alpha-adrenergic receptor agonist, and the alpha-adrenergic receptor agonist is tamsulosin. In some embodiments, the therapeutic agent includes the phosphodiesterase type 5 inhibitor, and the phosphodiesterase type 5 inhibitor is vardenafil.

The locally administering into the ureter may be achieved by any known means, including those that permit controllable release. For example, the local administration may be achieved with a cystoscope, a hydrogel, a lubricant, a retention matrix, a delayed release capsule, direct instillation, surgical irrigation, a catheter, a single compartment drug delivery device, an infusion pump, a drug pump, a drug eluting stent, a multi-compartment drug delivery device, an implanted drug delivery device, or a combination thereof.

In some embodiments, the locally administering into the ureter of a patient includes inserting a distal end portion of a transurethral catheter into the ureter; and releasing the formulation from the distal end portion of the catheter and into a lumen of the ureter.

In some embodiments, the locally administering into the ureter of a patient includes inserting a ureteral stent into the ureter, wherein the formulation is associated with, e.g., part of, the ureteral stent. The formulation, for example, may be in the form of a continuous or discontinuous coating on the ureteral stent. The ureteral stent may provide controlled release of the therapeutic agent.

In some embodiments, a formulation that is not operably associated with a ureteral stent is locally administered into a ureter of a patient before, during, and/or after the insertion of a ureteral stent into the ureter. The ureteral stent may or may not be associated with a portion of the formulation. For example, a formulation that is not operably associated with a ureteral stent may be locally administered into a ureter prior to insertion of a ureteral stent into the ureter, and the ureteral stent may include a formulation that is in the form of a continuous or discontinuous coating on the ureteral stent.

The methods, compositions, and systems herein may expose a ureter to a therapeutically effective amount of a therapeutic agent. A "therapeutically effective" amount can include an amount of composition effective to relax the ureteral smooth muscle to a degree and for a time effective to provide therapy for one or more genitourinary conditions, such as a urinary stone lodged in the ureter, ureteral colic, inflammation of the ureter, pain from ureteral stent, or a combination thereof.

Generally, a ureter may be exposed to any concentration of a calcium channel blocker and/or to any concentration of a rho kinase inhibitor. The concentrations may be limited only by one or more characteristics of a formulation (such as the compatibility of a matrix material and therapeutic agent), concerns regarding safety, or a combination thereof. In some embodiments, the therapeutic agent of the compositions, systems, and methods herein include a calcium channel blocker. A ureter may be exposed to the calcium channel blocker at a concentration of about 0.1 µM to about 1000 µM, about 0.1 µM to about 900 µM, about 0.1 µM to about 800 µM, about 0.1 µM to about 700 µM, about 0.1 µM to about 600 µM, about 0.1 µM to about 500 µM, about 0.1 µM to about 400 µM, about 0.1 µM to about 300 µM, about 0.1 µM to about 200 µM, or about 0.1 µM to about 150 µM.

In some embodiments, the therapeutic agent of the compositions, systems, and methods herein includes a rho kinase inhibitor. A ureter may be exposed to the rho kinase inhibitor at a concentration of about 0.1 µM to about 1000 µM, about 0.1 µM to about 900 µM, about 0.1 µM to about 800 µM, about 0.1 µM to about 700 µM, about 0.1 µM to about 600 µM, about 0.1 µM to about 500 µM, about 0.1 µM to about 400 µM, about 0.1 µM to about 300 µM, about 0.1 µM to about 200 µM, or about 0.1 µM to about 150 µM.

In some embodiments, the therapeutic agent of the compositions, systems, and methods herein includes a calcium channel blocker and a rho kinase inhibitor. A ureter may be exposed to the calcium channel blocker at a concentration of about 0.1 µM to about 1000 µM, about 0.1 µM to about 900 µM, about 0.1 µM to about 800 µM, about 0.1 µM to about 700 µM, about 0.1 µM to about 600 µM, about 0.1 µM to about 500 µM, about 0.1 µM to about 400 µM, about 0.1 µM to about 300 µM, about 0.1 µM to about 200 µM, or about 0.1 µM to about 150 µM. A ureter may be exposed to the rho kinase inhibitor at a concentration of about 0.1 µM to about 1000 µM, about 0.1 µM to about 900 µM, about 0.1 µM to about 800 µM, about 0.1 µM to about 700 µM, about 0.1 µM to about 600 µM, about 0.1 µM to about 500 µM, about 0.1 µM to about 400 µM, about 0.1 µM to about 300 µM, about 0.1 µM to about 200 µM, or about 0.1 µM to about 150 µM.

In some embodiments, the therapeutic agent of the compositions, systems, and methods herein includes a calcium channel blocker and a rho kinase inhibitor. The ureter may be exposed to the calcium channel blocker at a concentration of about 0.1 µM to about 30 µM, or about 0.1 µM to about 25 µM. The ureter may be exposed to the rho kinase inhibitor at a concentration of about 0.1 µM to about 60 µM, or about 0.1 µM to about 50 µM.

In some embodiments, the ureter is exposed simultaneously to the calcium channel blocker at a concentration of about 0.5 µM to about 0.15 µM, and the rho kinase inhibitor at a concentration of about 10 µM to about 30 µM.

In some embodiments, the ureter is exposed simultaneously to the calcium channel blocker at a concentration of about 0.15 µM to about 0.25 µM, and the rho kinase inhibitor at a concentration of about 1.5 µM to about 50 µM.

In some embodiments, the ureter is exposed simultaneously to the calcium channel blocker at a concentration of about 0.35 µM to about 0.45 µM, and the rho kinase inhibitor at a concentration of about 1.5 µM to about 30 µM.

In some embodiments, the ureter is exposed simultaneously to the calcium channel blocker at a concentration of about 0.7 µM to about 0.9 µM, and the rho kinase inhibitor at a concentration of about 1.5 µM to about 30 µM.

In some embodiments, the ureter is exposed simultaneously to the calcium channel blocker at a concentration of about 1.3 µM to about 1.7 µM, and the rho kinase inhibitor at a concentration of about 3 µM to about 30 µM.

In some embodiments, the ureter is exposed simultaneously to the calcium channel blocker at a concentration of about 2.5 µM to about 3.5 µM, and the rho kinase inhibitor at a concentration of about 1.5 µM to about 50 µM.

In some embodiments, the ureter is exposed simultaneously to the calcium channel blocker at a concentration of about 4 µM to about 8 µM, and the rho kinase inhibitor at a concentration of about 1.5 µM to about 50 µM.

In some embodiments, the ureter is exposed simultaneously to the calcium channel blocker at a concentration of about 10 µM to about 15 µM, and the rho kinase inhibitor at a concentration of about 0.75 µM to about 15 µM.

In some embodiments, the ureter is exposed simultaneously to the calcium channel blocker at a concentration of about 0.1 µM to about 3.2 µM, and to the rho kinase inhibitor at a concentration of about 1.5 µM to about 50 µM.

In some embodiments, the ureter is exposed simultaneously to the calcium channel blocker at a concentration of about 0.1 µM to about 1.6 µM, and to the rho kinase inhibitor at a concentration of about 3.0 µM to about 25 µM.

In some embodiments, the ureter is exposed simultaneously to the calcium channel blocker at a concentration of about 0.1 µM to about 6.25 µM, and to the rho kinase inhibitor at a concentration of about 0.75 µM to about 12.5 µM.

In some embodiments, the therapeutic agent of the compositions, systems, and methods herein includes an alpha-adrenergic receptor agonist, a phosphodiesterase type 5 inhibitor, or a combination thereof. A ureter may be exposed to the alpha-adrenergic receptor agonist at a concentration of about 0.5 µM to about 3.0 µM. A ureter may be exposed to the phosphodiesterase type 5 inhibitor at a concentration of about 4 µM to about 8 µM. In some embodiments, a ureter is simultaneously exposed to the alpha-adrenergic receptor agonist at a concentration of about 0.5 µM to about 3.0 µM, and the phosphodiesterase type 5 inhibitor at a concentration of about 4 µM to about 8 µM.

Drug Delivery Systems

Drug delivery systems are provided herein. In embodiments, the drug delivery systems include a delivery device having at least a part thereof which is configured for insertion into a ureter of a patient; and a formulation including a therapeutic agent selected from a calcium channel blocker, a rho kinase inhibitor, or a combination thereof, wherein the delivery device is configured to deliver the therapeutic agent to the ureter in an amount effective to relax ureteral smooth muscle in vivo.

In some embodiments, the drug delivery systems include a delivery device that provides prolonged exposure of the therapeutic agent to the ureter. For example, a ureter may be exposed to the therapeutic agent for a period lasting at least 30 minutes, one hour, two hours, etc. In some embodiments, the delivery device provides prolonged exposure of the therapeutic agent to the ureter for a period of about 0.5 days to about 3 days, about 1 day to about 7 days, or about 1 day to about 30 days.

The drug delivery systems may include one or more components or features that permit controllable release. For example, the drug delivery systems may include a cystoscope, a retention matrix, a delayed release capsule, surgical irrigation, a catheter, a single compartment drug delivery device, an infusion pump, a drug pump, a drug eluting stent, a multi-compartment drug delivery device, an implanted drug delivery device, or a combination thereof.

In some embodiments, the drug delivery systems include a transurethral catheter having a distal end portion configured for insertion into a ureter. A formulation may be discharged from the distal end portion into a ureter.

Figure 12:
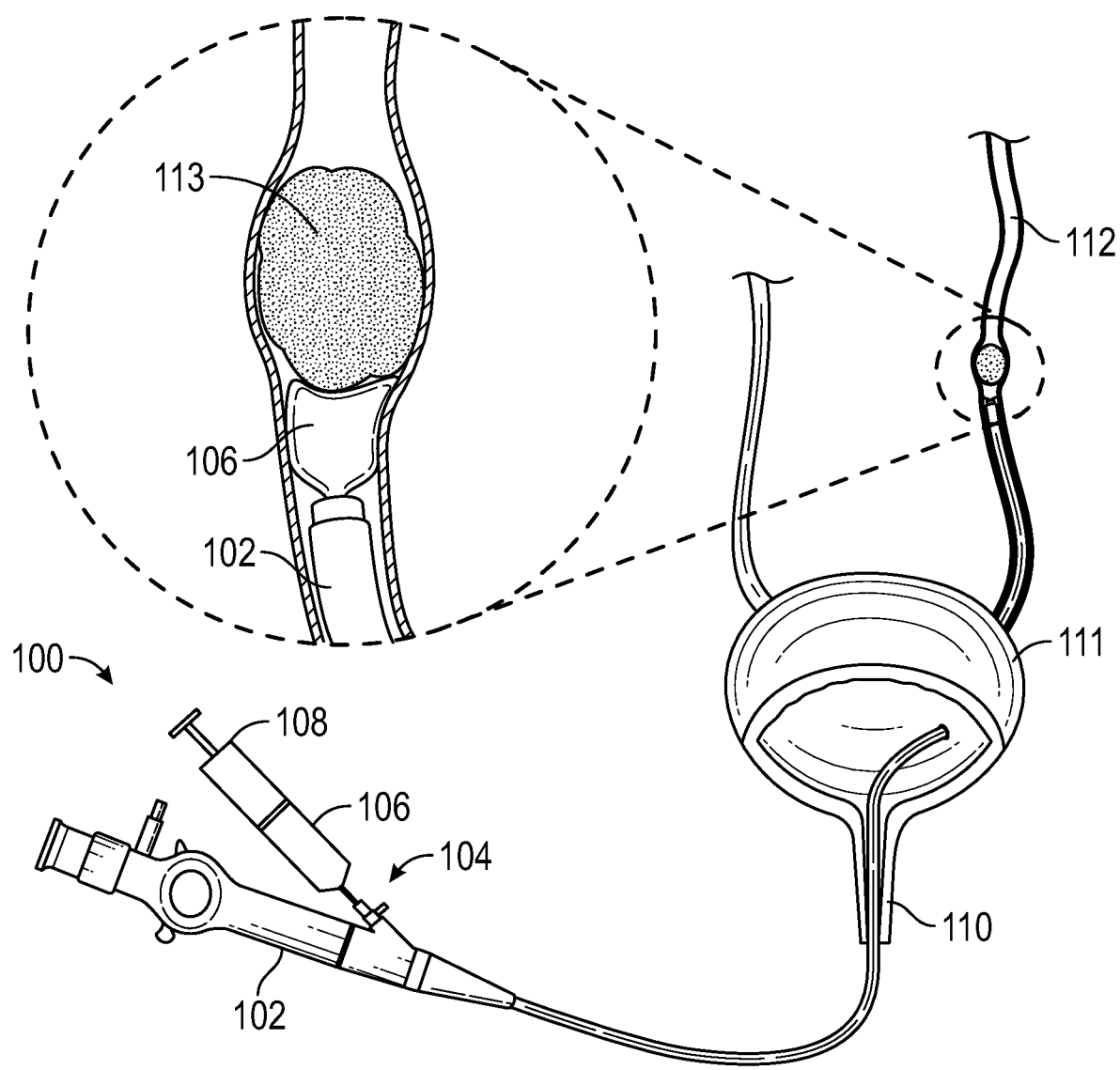
FIG. 12 depicts an embodiment of a drug delivery system.

An embodiment of a drug delivery system 100 is depicted at FIG. 12. The drug delivery system 100 includes a ureteroscope 102 that can be inserted into a urethra 110, through a bladder 111, and into a ureter 112 in which a ureteral stone 113 is lodged. A therapeutic agent formulation supply 104 is associated with the ureteroscope 102. A syringe 108 may push the therapeutic agent formulation 106 through and out of the ureteroscope 102 and into the ureter 112. The drug delivery system 100 may deliver the therapeutic agent formulation 106 to a region of the ureter 112 that is adjacent to the ureteral stone 113, and at least a portion of the therapeutic agent formulation 106 may, upon delivery, contact the ureteral stone 113.

In some embodiments, the drug delivery systems include a ureteral stent, wherein a formulation is associated with, e.g., part of, the ureteral stent. The formulation, for example, may be in the form of a continuous or discontinuous coating on the ureteral stent. The ureteral stent may provide controlled release of the therapeutic agent.

The terms "a," "an," and "the" are intended to include plural alternatives, e.g., at least one. For instance, the disclosure of "a therapeutic agent," "an excipient," and the like, is meant to encompass one, or mixtures or combinations of more than one therapeutic agent, excipient, and the like, unless otherwise specified.

In the descriptions provided herein, the terms "includes," "is," "containing," "having," and "comprises" are used in an open-ended fashion, and thus should be interpreted to mean "including, but not limited to." When methods or systems are claimed or described in terms of "comprising" various components or steps, the methods or systems can also "consist essentially of" or "consist of" the various components or steps, unless stated otherwise.

Various numerical ranges may be disclosed herein. When Applicant discloses or claims a range of any type, Applicant's intent is to disclose or claim individually each possible number that such a range could reasonably encompass, including end points of the range as well as any sub-ranges and combinations of sub-ranges encompassed therein, unless otherwise specified. Moreover, all numerical end points of ranges disclosed herein are approximate. As a representative example, Applicant discloses, in one embodiment, that a ureter is exposed to a rho kinase inhibitor at a concentration of about 3 µM to about 30 µM. This range should be interpreted as encompassing values in a range of about 3 µM to about 30 µM, and further encompasses "about" each 4 µM, 5 µM, 6 µM, 7 µM, 8 µM, 9 µM, 10 µM, 11 µM, 12 µM, 13 µM, 14 µM, 15 µM, 16 µM, 17 µM, 18 µM, 19 µM, 20 µM, 21 µM, 22 µM, 23 µM, 24 µM, 25 µM, 26 µM, 27 µM, 28 µM, and 29 µM, including any ranges and sub-ranges between any of these values.

The processes described herein may be carried out or performed in any suitable order as desired in various implementations. Additionally, in certain implementations, at least a portion of the processes may be carried out in parallel. Furthermore, in certain implementations, less than or more than the processes described may be performed.

Many modifications and other implementations of the disclosure set forth herein will be apparent having the benefit of the teachings presented in the foregoing descriptions and the associated drawings. Therefore, it is to be understood that the disclosure is not to be limited to the specific implementations disclosed and that modifications and other implementations are intended to be included within the scope of the appended claims

EXAMPLES

The present invention is further illustrated by the following examples, which are not to be construed in any way as imposing limitations upon the scope thereof. On the contrary, it is to be clearly understood that resort may be had to various other aspects, embodiments, modifications, and equivalents thereof which, after reading the description herein, may suggest themselves to one of ordinary skill in the art without departing from the spirit of the present invention or the scope of the appended claims. Thus, other aspects will be apparent to those skilled in the art from consideration of the specification and practice of the invention disclosed herein.

Example 1—High Throughput Screening (HTS) for Determining Therapeutic Candidates for Ureteral Relaxation An HTS test was developed to quantify the contractile state of a human ureteral smooth muscle cell (hUSMC). Quantification of hUSMC relaxation was achieved by performing single-cell analysis using a computer vision (Cell-Profiler, Broad Institute, MA) approach that related each cell's fluorescence intensity to its state of muscle relaxation (comparing phosphorylated myosin with unphosphorylated myosin).

Primary hUMSCs were harvested from patients and cultured. There were about 10,000 cells per well, and 100 μL of media per well. Each well represented one experiment, and 250 nL of drug per well was delivered with DMSO (0.25% DMSO by volume).

In the test of this example, single cell analysis was performed on each cell (identified via computer vision) after exposure to various drugs which enable relaxation in order to correlate each cell's contractile state to the therapeutic compound, exposure time, and dose.

These correlations were determined by analyzing the fluorescent intensity of smooth muscle cells, which is related to the contractile state of the muscles. When a smooth muscle cell is signaled to contract, phosphorylation of myosin light-chain (p-MLC) occurs, which is a biomarker of muscle contraction. Conversely, when smooth muscle is left unphosphorylated (MLC), muscle relaxation occurs. Therefore, smooth muscle contraction can be computed from the proportion of p-MLC to unphosphorylated-MLC.

Representative agents which induce smooth muscle relaxation from an all-encompassing screen were used to discern lead compounds after assaying over 900M individual cells for timing and dose. The tested agents included those in the following table.

TABLE 1

Agents Subjected to HTS of Example 1

| Class | Drug | Molecular Weight (g/mol) |
|---|---|---|
| α-Adrenoceptor Agonists | Tamsulosin (HCl) | 444.97 |
| β-Adrenoceptor Agonists | Isoproterenol | 247.7 |
| | Butoxamine (HCl) | 303.82 |
| | Mirabegron | 396.5 |
| Phosphodiesterase (PDE) Inhibitors | Sildenafil | 474.6 |
| | Vardenafil | 579.1 |
| | Rolipram | 275.3 |
| Calcium Channel Blocker | Nifedipine | 346.3 |
| Rho-Kinase Inhibitor | Y-27632 (HCl) | 320.3 |
| Prostaglandin (PG) & COX | Prostaglandin E1 | 354.5 |
| | Prostaglandin E2 | 352.5 |
| | Diclofenac (Sodium) | 318.1 |
| | Celecoxib | 381.4 |
| Seratonin (5-HT) | Ondansetron (HCl) | 329.8 |
| Nitric Oxide (NO) Donors | L-Arginine | 219.2 |
| Anticholinergic Bronchodilator | Tiotropium | 472.4 |
| Antiarrhythmic Agent | Adenosine | 267.24 |
| Muscarinic Acetylcholine Receptor Antagonist | Atropine | 289.3 |

For the agents listed at Table 1, smooth muscle relaxation was correlated to therapeutic class and dose. Eight-point dosing curves were performed starting at 25 μM. Cell viability was maintained at 80% or greater for all sample points. The results were collected from three separate screening runs across three unique primary hUSMC lines (derived from three separate patients).

Celecoxib, nifedipine, and ROCK Y-27632 all demonstrated significant relaxation of smooth muscle compared to all other screened drug agents at prolonged exposure (8 hours), while tamsulosin and vardenafil demonstrated efficacy at certain doses as well. A 3.13 μM exposure of Y-27632 was able to relax 20% of smooth muscle cells within a cell population (a controlled cell culture well). Increasing the exposure to 25 μM yielded greater than 40% relaxation. A 3.13 μM exposure to nifedipine also led to 20% relaxation and increasing the exposure to 25 μM resulted in greater than 40% relaxation as well. Celecoxib achieved 20% relaxation at 12.5 μM and increasing to 25 μM led to 30% relaxation. These relaxation percentages were derived after an 8 hour exposure. Tamsulosin and vardenafil also yielded ~20% cell population relaxation at micromolar screening and dosing at 6.25 μM and 1.56 μM or greater, respectively. Despite the data of this example, it was discovered that celecoxib likely was a "false hit", because the observed relaxation was apparently caused by the fact that celecoxib's toxicity killed the tested cells.

The results for all of the agents tests in this example are depicted at FIG. 1.

Figure 2:
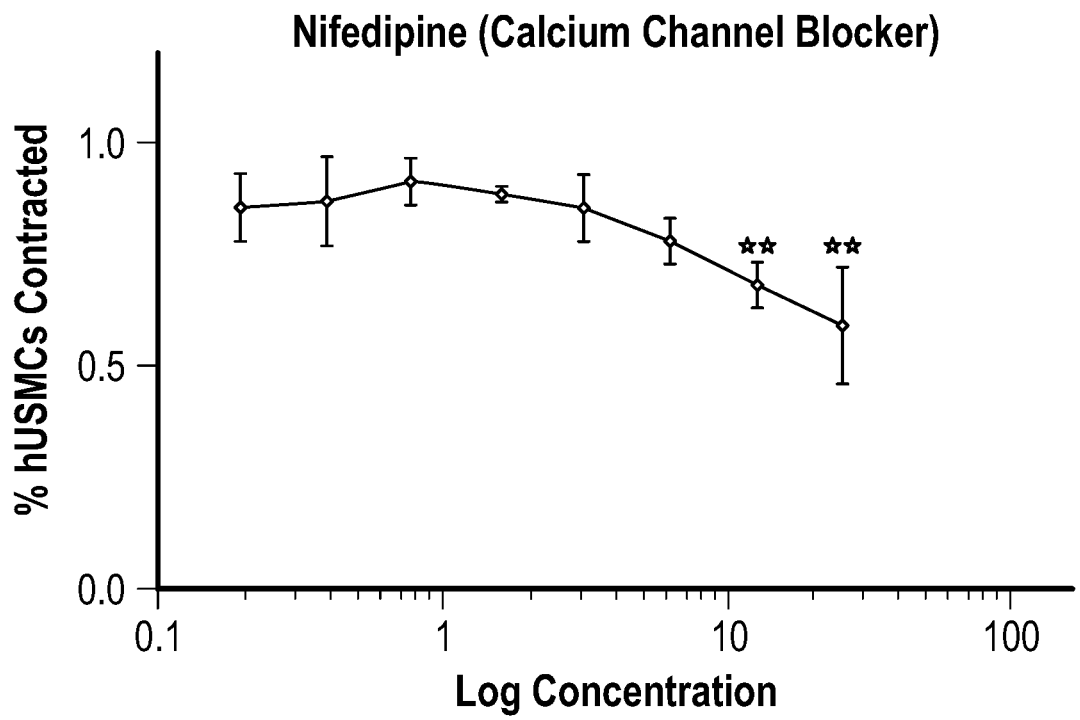
FIG. 2 depicts the effect of nifedipine (calcium channel blocker) on smooth muscle relaxation, according to the test of Example 1.
Figure 3:
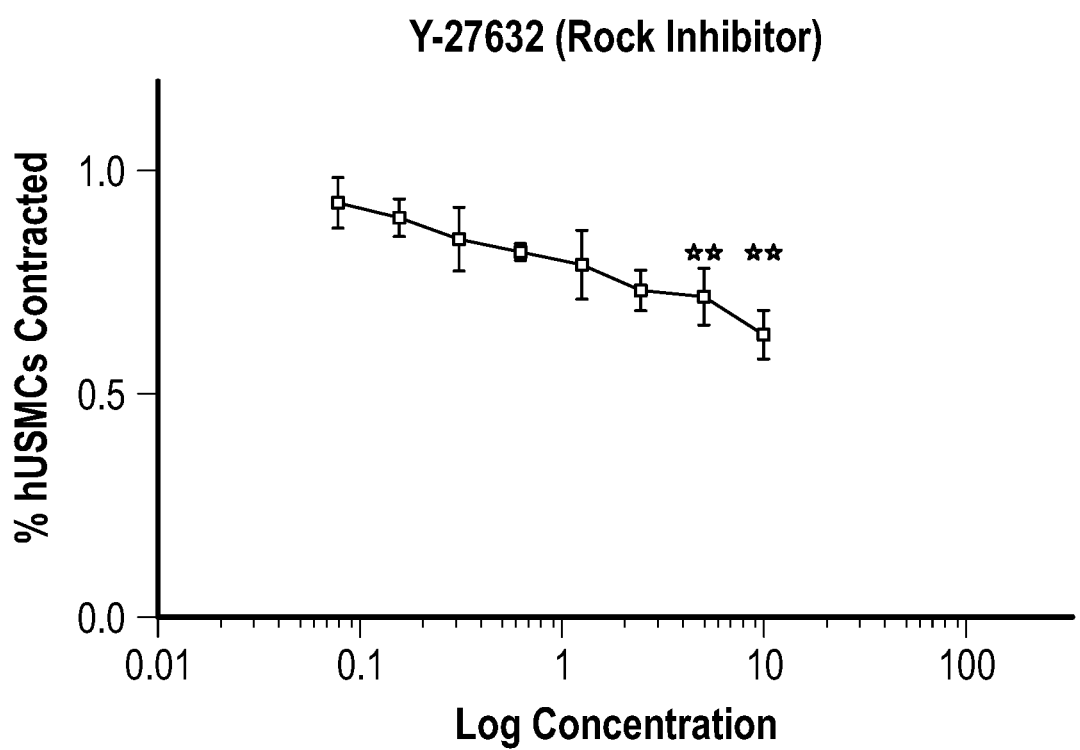
FIG. 3 depicts the effect of Y-27632 (rho kinase inhibitor) on smooth muscle relaxation, according to the test of Example 1.
Figure 4:
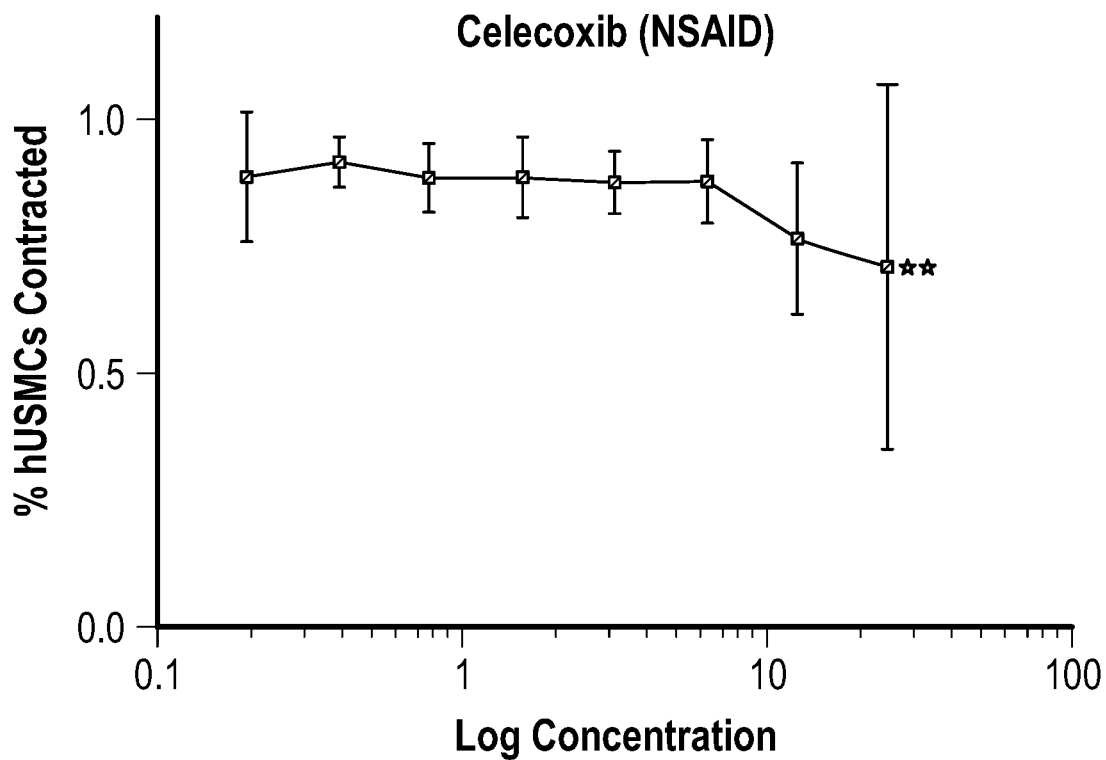
FIG. 4 depicts the effect of celecoxib on smooth muscle relaxation, according to the test of Example 1.

FIG. 1 demonstrates that Y-27632 (ROCK), Nifedipine, and Celecoxib led to relatively significant cell relaxation in this test, with ROCK and Nifedipine having the greatest effect—relaxing about 40% of the hUSMC population after an 8 hour exposure. The results obtained with these three therapeutic agents, with error bars, are depicted at FIG. 2 (Nifedipine), FIG. 3 (ROCK), and FIG. 4 (Celecoxib).

Example 2—Analysis of Drug Synergy and Cell Viability

The screening of this example showed that synergy was achieved by dosing several agents simultaneously.

For example, the therapeutic agents ROCK and Nifedipine were co-exposed to hUSMCs at various concentrations, and the results of this test demonstrated that these therapeutic agents exhibited a synergistic effect on muscle contraction.

Via a local approach, 25 µM of nifedipine alone led to 45% relaxation after an 8 hour exposure, and 25 µM of ROCK Y-27632 also resulted in a relaxation of about 45% after an 8 hour exposure. Delivering a combination of 25 µM/25 µM nifedipine/ROCK Y-27632, however, resulted in a relaxation of nearly 75% at 8 hours, which was a 166% improvement over single drug exposure.

The results of the test of this example are depicted at Table 2, which provides the percentages of cells that remained contracted after exposure to the two simultaneous dosing schemes. Table 2 presents averaged data from across 5 unique primary cell lines (N=5).

TABLE 2

Percentages of Cells that Remained Contracted After Treatment

| | | Nifedipine Concentration (µM) | | | | | | | | | |
|---|---|---|---|---|---|---|---|---|---|---|---|
| | | 25.00 | 12.50 | 6.25 | 3.13 | 1.56 | 0.78 | 0.39 | 0.20 | 0.10 | 0 |
| ROCK Conc. (µM) | 50.00 | 26% ** | 26% ** | 34% ** | 47% * | 49% * | 50% | 47% * | 49% * | 51% | 50% |
| | 25.00 | 25% ** | 31% ** | 39% ** | 47% * | 52% * | 51% * | 52% | 56% | 54% | 54% |
| | 12.50 | 26% ** | 38% ** | 47% * | 54% * | 60% | 58% * | 60% | 57% * | 60% | 59% |
| | 6.25 | 29% ** | 46% ** | 56% ** | 62% * | 67% | 66% * | 68% | 64% * | 67% | 67% |
| | 3.13 | 31% ** | 57% ** | 67% * | 71% | 73% | 71% | 70% * | 75% | 71% |
| | 1.56 | 36% ** | 71% * | 73% * | 80% * | 79% * | 73% * | 75% | 78% * | 79% * | 81% |
| | 0.78 | 39% ** | 78% * | 91% | 89% | 86% | 85% * | 88% | 86% | 87% | 86% |
| | 0 | 55% | 100% | 101% | 106% | 99% | 102% | 102% | 103% | 102% | 99% |

The percentages shown at Table 2 were values averaged from five separate runs on five unique primary human cell lines.

Synergy (i.e., where the combined effect was greater than the individual effect) was observed in multiple dosing points (denoted with "*"). Conditions where significant synergy is seen (i.e., where the effect was more prominently observed) is denoted with "**".

As shown at Table 2, the combinatorial effects demonstrated significance when there were fewer cells which remained in a contractile state compared to delivery of each compound alone.

Cell viability in each well was at least 87%. The percentages of cells that retained viability are provided at Table 3 for the corresponding results in Table 2.

TABLE 3

Percentages of Cells that Retained Viability

| | | Nifedipine Concentration (µM) | | | | | | | | | |
|---|---|---|---|---|---|---|---|---|---|---|---|
| | | 25.00 | 12.50 | 6.25 | 3.13 | 1.56 | 0.78 | 0.39 | 0.20 | 0.10 | 0 |
| ROCK Conc. (µM) | 50.00 | 90% | 87% | 94% | 90% | 94% | 97% | 100% | 98% | 98% | 95% |
| | 25.00 | 94% | 96% | 95% | 102% | 106% | 107% | 108% | 103% | 106% | 100% |
| | 12.50 | 93% | 94% | 103% | 106% | 107% | 108% | 109% | 110% | 102% | 103% |
| | 6.25 | 99% | 99% | 107% | 108% | 105% | 111% | 110% | 111% | 105% | 109% |
| | 3.13 | 97% | 103% | 109% | 105% | 107% | 112% | 110% | 107% | 106% | 110% |
| | 1.56 | 100% | 102% | 109% | 109% | 109% | 111% | 113% | 110% | 111% | 106% |
| | 0.78 | 94% | 99% | 105% | 106% | 108% | 114% | 109% | 112% | 110% | 108% |
| | 0 | 91% | 98% | 97% | 99% | 102% | 100% | 102% | 102% | 102% | 105% |

As shown at Table 3, viabilities of less than 90% were rarely observed. Viabilities exceeding 100% are due to variations in cell populations that were plated.

Example 3—Bench Top Ex Vivo Model

The lead therapeutics were then validated on an organ level using an ex vivo bench-top model that relied on whole porcine ureters. The ex vivo model demonstrated that manipulation (and reversal) of ureteral physiology could be achieved via pharmacological delivery alone.

Using an ex vivo model, the dosages found to be effective in vitro were verified. Exposing a pig ureter to 10 µM of nifedipine and 10 µM of ROCK Y-27632 intraluminally resulted in complete cessation of contractile activity and a 3× reduction in contractile frequency, respectively. These results verified the in vitro screening findings of Example 2.

An ex vivo bench top model was designed to permit the testing of whole ureteral segments. Flow through the ureteral segments was regulated, and ranged from 0.25 mL/minute to 60 mL/minute. A mixture of 95% oxygen and 5% carbon dioxide (carbogen) was bubbled through the organ bath, which contained standard isotonic buffer solution heated to physiological temperature of 37° C. The intraluminal reservoirs contained either preheated saline buffer or dilutions of any candidate therapeutic agent. Proof-of-concept at an organ level could be demonstrated with this system.

Figure 5:
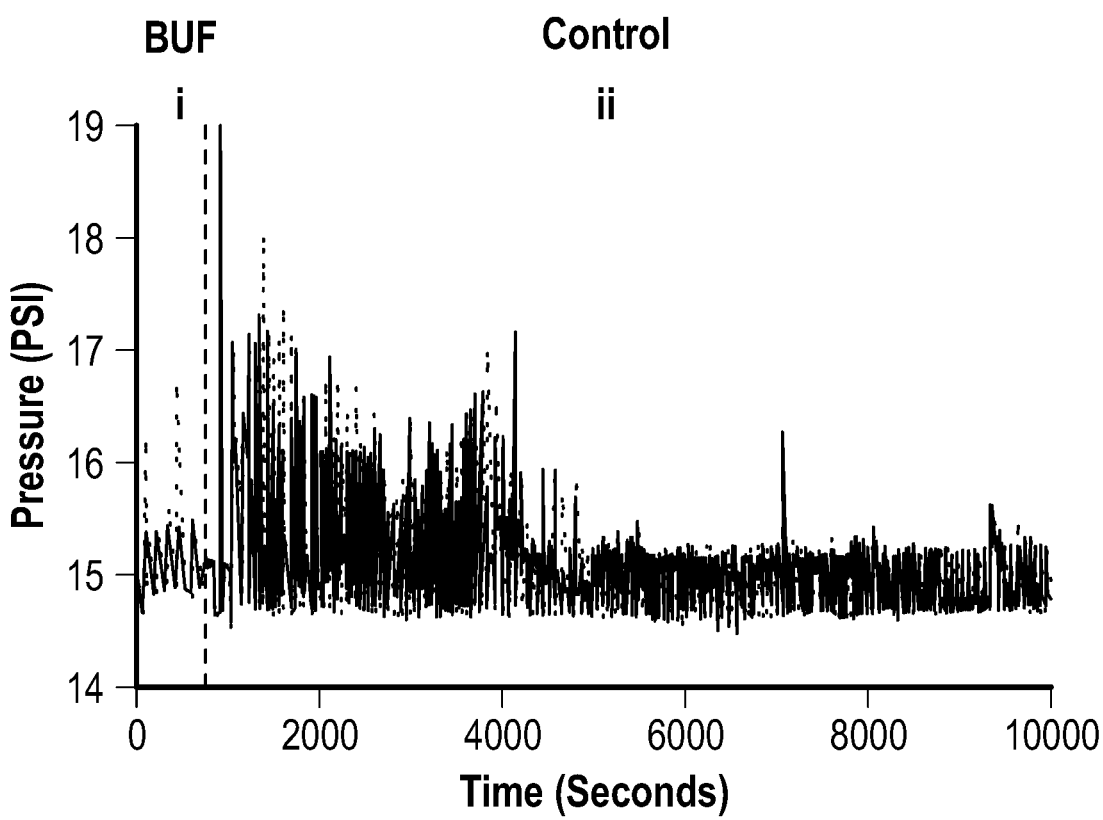
FIG. 5 depicts pressure readings collected from an embodiment of an ex vivo model in which contractions were pharmacologically replicated in ureteral segments.

The ex vivo model of this example pharmacologically replicated contractions seen in the ureter due to an obstruction. Truncated data is depicted at FIG. 5, in which "BUF" corresponds to the delivery of saline (region "i"). Baseline peristalsis was achieved by eluting phenylephrine (10 mM, about 1 mL/minute) (Control) through the intraluminal space, where consistent contractions were seen for 5+ hours (18,000 seconds). One contraction was observed approximately every 20-30 seconds. The pounds per square inch (PSI) pressure readings were obtained using a fiber-optic pressure catheter.

Figure 6:
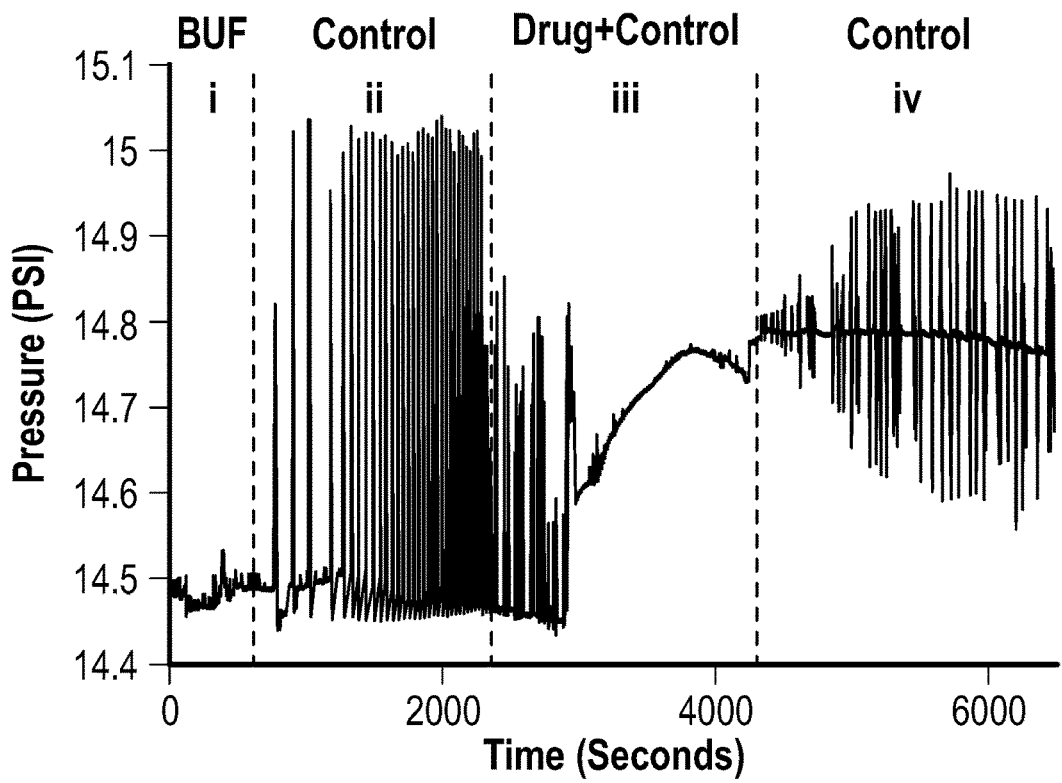
FIG. 6 depicts data collected from a test described herein in which nifedipine was administered to a ureter.

The promotion of ureteral relaxation via intraluminal delivery of nifedipine (calcium channel blocker) also tested, as depicted at FIG. 6. For this test, a ureter was prepared through intraluminal delivery of saline (Krebs-Henseleit Buffer) (BUF) only (region "i"). The experiment then was initiated and phenylephrine [10 mM] was added to the Krebs infusion to stimulate baseline peristaltic contractions seen in patients with urinary stones (region "ii"). Nifedipine [10 μM] was introduced to the saline and 10 mM phenylephrine infusion, and rapid relaxation of the ureter was achieved (region "iii"). The plot at region iii indicated a rapid cessation of contractions. [1 μM] Nifedipine then was removed from the infusion, and the effects were reversed (region "iv"). The baseline contractions were seen again at region iv with the [10 mM] phenylephrine and saline buffer. Similar effects were observed upon the delivery of ROCK.

Figure 7:
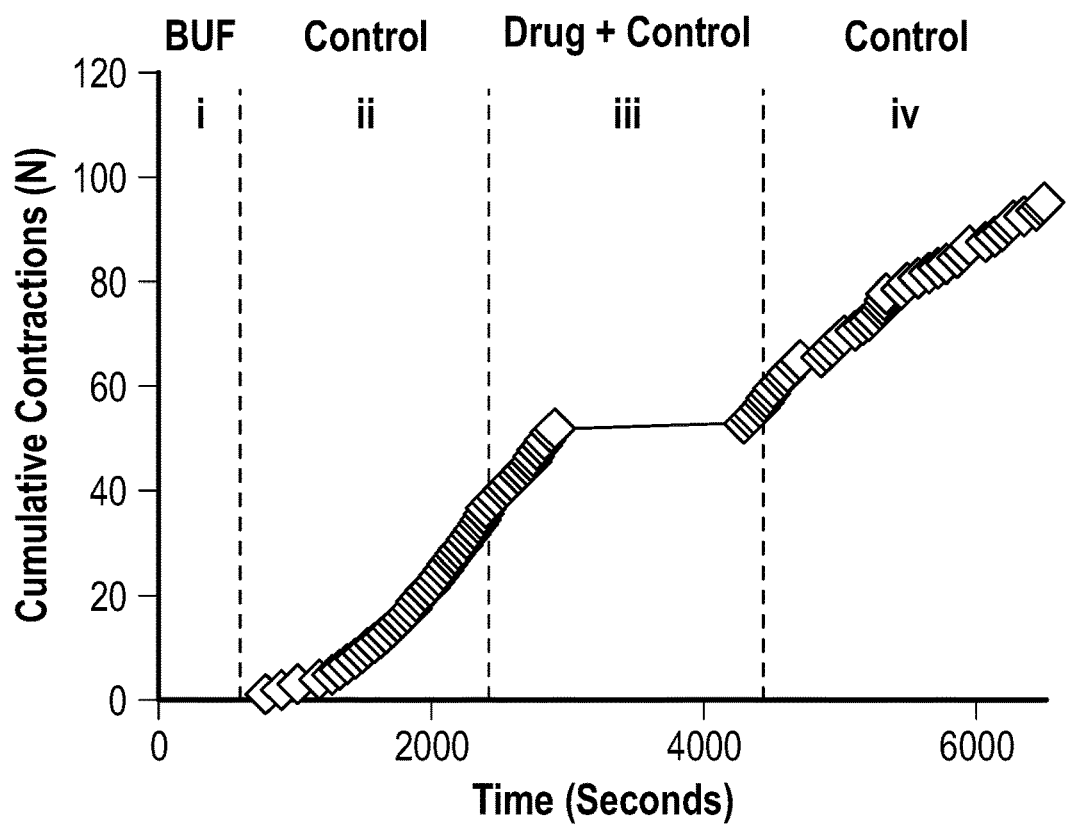
FIG. 7 depicts a plot of cumulative ureteral contractions observed during a test described herein.

During the experiment that generated the data of FIG. 6, cumulative ureteral contractions were plotted, as depicted at FIG. 7.

Figure 8:
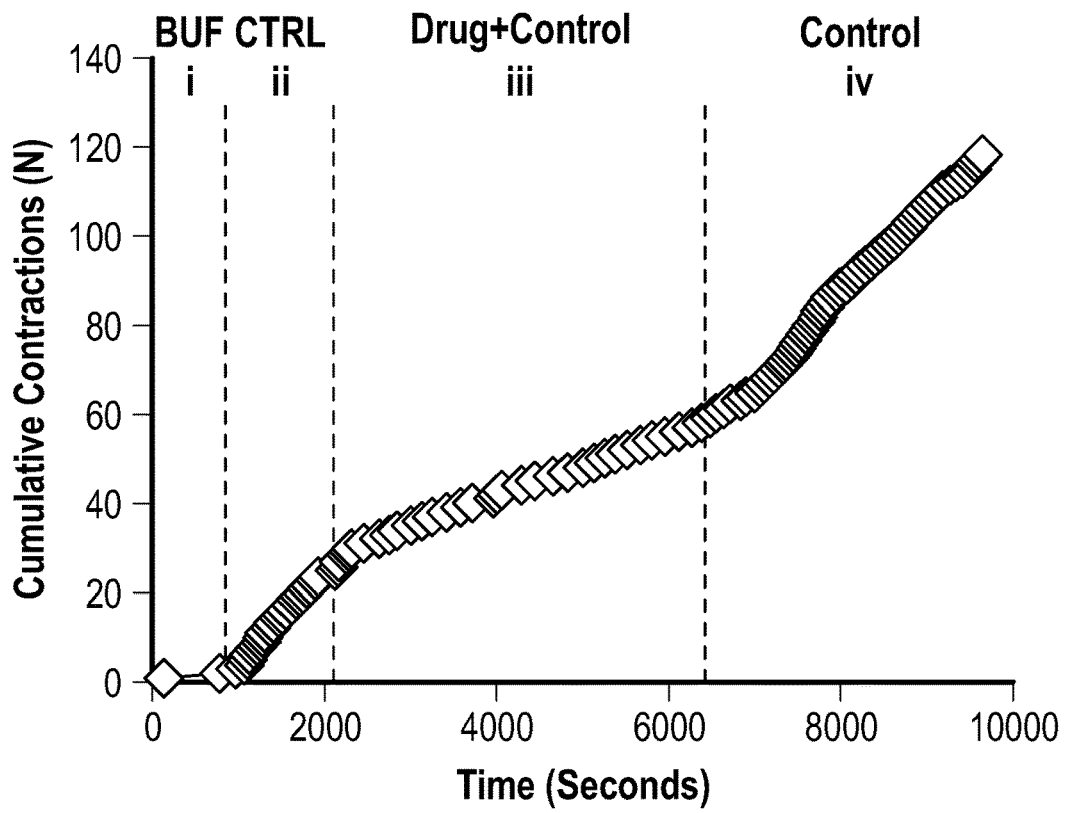
FIG. 8 depicts a plot of cumulative ureteral contractions observed during a test described herein.

A similar effect was observed when ROCK was delivered directly to the lumen of an ex vivo pig ureter. Cumulative ureteral contractions were plotted over the course of the entire experiment, and are depicted at FIG. 8. For this test, a ureter was prepared through intraluminal delivery of saline (BUF) only (region "i"). The experiment was initiated and phenylephrine [10 mM] was added to the Krebs infusion to stimulate baseline peristaltic contractions seen in patients with urinary stones (region "ii"). Y27632 (ROCK) [10 μM] was introduced to the saline and 10 mM phenylephrine infusion, and rapid relaxation of the ureter was observed (region "iii"). Though cessation of peristatic activity was not entirely arrested, there was a significant decrease in frequency. 10 μM Y27632 (ROCK) was removed from the infusion, and the effects were reversed (region "iv"). The baseline contractions were once again observed with [10 mM] phenylephrine and saline buffer.

Since cessation was not observed upon administration of ROCK, a linear regression on each of the regions was performed, and indicated that there was at least a 3× reduction seen in the slope, with high $R^2$ correlation.

TABLE 4

Linear Regression of Regions i-iv of FIG. 8
Linear Regression of Regions

| Region | Linear Regression | $R^2$ |
|---|---|---|
| Region ii | y = 0.0224x − 19.247 | 0.9859 |
| Region iii | y = 0.0068x + 14.451 | 0.9976 |
| Region iv | y = 0.0194x − 59.444 | 0.9995 |

Complete cessation would likely have been achievable with increased dose of ROCK. A return to baseline level frequency was observed in region "iv".

Example 4—Delivery of Therapeutic Agent in Pig Ureters

A commercially available surgical lubricant (SURGI-LUBE® lubricant) was combined with a surfactant. The surfactant was Polysorbate 20, and 0.6 mL of the Polysorbate 20 was added to 19.4 mL of the surgical lubricant. The surfactant was added because the therapeutic agent of this example had a relatively low solubility in the water-based lubricant.

To the surgical lubricant/surfactant mixture, 100 μL of ROCKi and 100 μL of nifedipine were added. The ROCKi and nifedipine solutions were pre-made at [1M] concentrations and dissolved in dimethylsulfoxide (DMSO). After the therapeutic agent was added, the actual drug retention in the surgical lubricant/surfactant mixture was about 200 μM for each component. However, more surfactant may be added to increase drug concentration, e.g., up to about 500 μM.

The surgical lubricant/surfactant mixture containing the therapeutic agent, and a control surgical lubricant/surfactant mixture that did not include a therapeutic agent were delivered into ex vivo adult female pig ureters.

Figure 9:
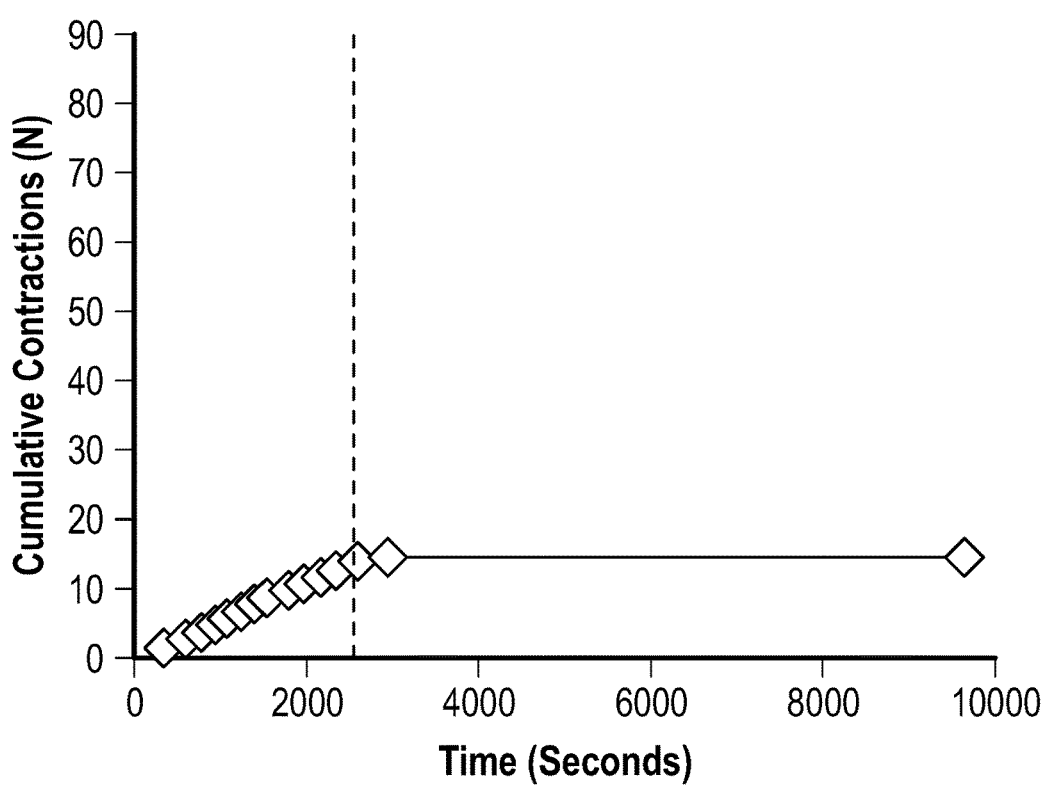
FIG. 9 depicts a plot of cumulative contractions of an ex vivo pig ureter after delivery of an embodiment of a formulation.
Figure 10:
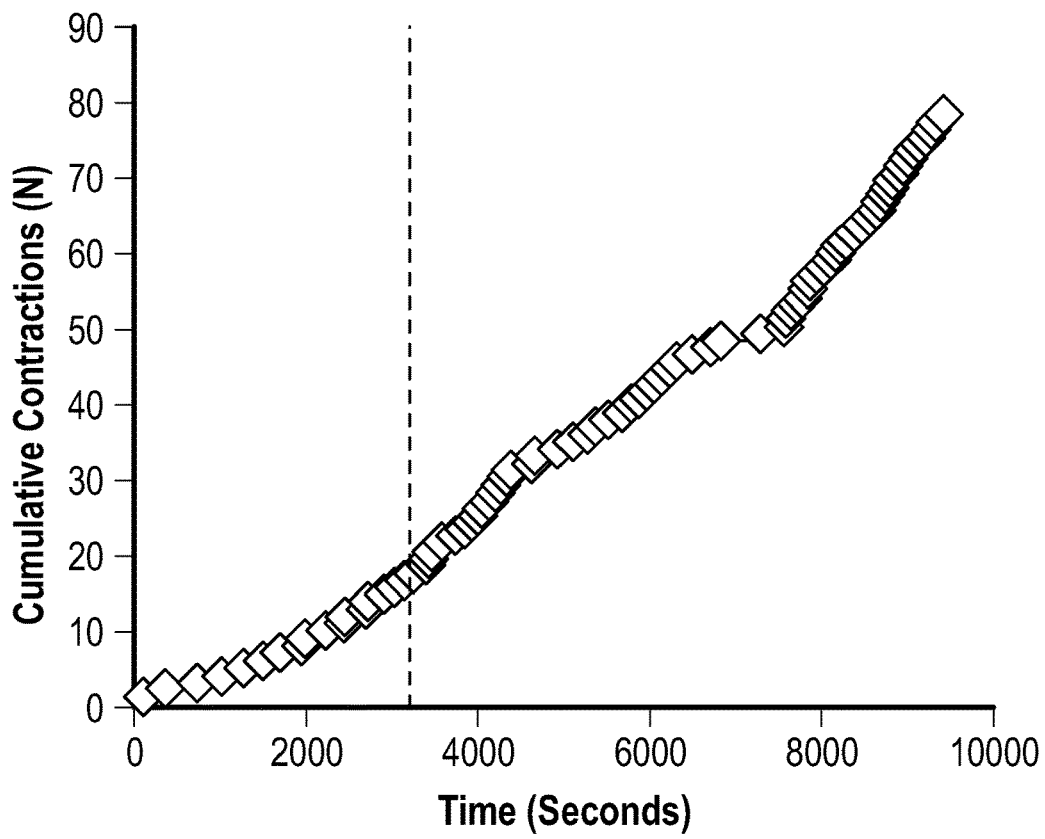
FIG. 10 depicts a plot of cumulative contractions of an ex vivo pig ureter after delivery of a control formulation.

As depicted at FIG. 9, contractions were halted by the surgical lubricant/surfactant mixture containing the therapeutic agent, but contractions were not arrested by the control surgical lubricant/surfactant, as shown at FIG. 10.

Example 5—In Vivo Testing

In vivo testing of the formulation of Example 4 also was conducted. A cytoscope was introduced through the urethral orifice, into the bladder of three pigs, and passed towards the ureterovesical junction (UVJ). A 5 Fr open-ended ureteral catheter was then passed through the working channel of the cytoscope into the lumen of the ureter. 5 mL of the surgical lubricant/surfactant/drug mixture was then deployed into the lumen of the ureter.

Immediately after deployment of drug formulation, a 0.9 Fr fiber optic pressure probe was introduced into the lumen of the 5 Fr catheter. The probe recorded continuous intraluminal pressure for 60 minutes for each condition, i.e., baseline, oral tamsulosin (tested on a separate day), and locally treated.

Characteristic peristaltic pressure data was recorded from within the lumen of the ureter in pounds per inch$^2$ (psi). Each recording was a continuous waveform representing 30 minutes of data acquisition.

Figure 11:
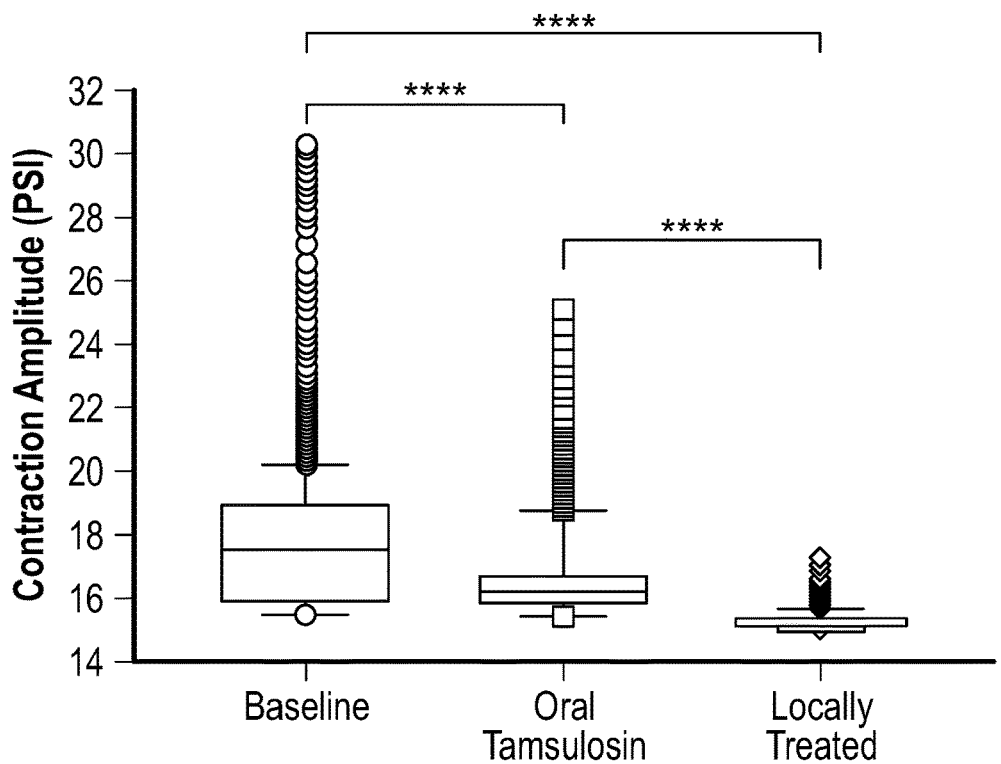
FIG. 11 depicts an analysis of the amplitude of waveforms depicted via box plots (5-95 percentile).

Local drug delivery resulted in significant reduction in contraction frequency and contractile amplitude of the ureter compared to baseline and oral "gold standard," tamsulosin. FIG. 11 depicts an analysis of the amplitude of waveforms depicted via box plots (5-95 percentile). Each category corresponds to the collective peak amplitude of contractions obtained from three individual pig specimens. Ureters which were treated locally in vivo saw significant reduction in contraction amplitude compared to both baseline and oral tamsulosin.

The invention claimed is:

1. A method for treating a patient having a genitourinary condition, the method comprising:
   locally administering into a ureter of the patient a formulation configured to delay passage of the formulation from the ureter, the formulation comprising a therapeutically effective amount of a therapeutic agent selected from a calcium channel blocker, a rho kinase inhibitor, or a combination thereof.

2. The method of claim 1, wherein the therapeutic agent comprises the calcium channel blocker and the rho kinase inhibitor.

3. The method of claim 1, wherein the calcium channel blocker is nifedipine.

4. The method of claim 1, wherein the rho kinase inhibitor is Y-27632.

5. The method of claim 1, wherein the genitourinary condition comprises a urinary stone in the ureter.

6. The method of claim 1, wherein the formulation is in the form of a viscous vehicle, the viscous vehicle comprising one or more pharmaceutically acceptable excipients, together with the therapeutic agent.

7. The method of claim 6, wherein the locally administering into the ureter of the patient comprises:
inserting a distal end portion of a catheter into the ureter; and
releasing the formulation from the distal end portion of the catheter and into a lumen of the ureter.

8. The method of claim 1, wherein the ureter is exposed to the calcium channel blocker at a concentration of about 0.1 µM to about 1000 µM.

9. The method of claim 1, wherein the ureter is exposed to the rho kinase inhibitor at a concentration of about 0.1 µM to about 1000 µM.

10. The method of claim 1, wherein the ureter is exposed simultaneously to the calcium channel blocker at a concentration of about 0.1 µM to about 3.2 µM, and to the rho kinase inhibitor at a concentration of about 1.5 µM to about 50 µM.

11. A method for relaxing human ureteral smooth muscle in vivo, the method comprising:
locally administering into a ureter of a patient a formulation configured to delay passage of the formulation from the ureter, the formulation comprising a therapeutically effective amount of a combination of a calcium channel blocker and a rho kinase inhibitor.

12. The method of claim 11, wherein (i) the calcium channel blocker is nifedipine, (ii) the rho kinase inhibitor is Y-27632, or (iii) the calcium channel blocker is nifedipine and the rho kinase inhibitor is Y-27632.

13. A method for relaxing human ureteral smooth muscle in vivo, the method comprising:
locally administering into a ureter of a patient a formulation configured to delay passage of the formulation from the ureter, the formulation comprising a therapeutically effective amount of a therapeutic agent selected from a calcium channel blocker, a rho kinase inhibitor, or a combination thereof.

14. The method of claim 13, wherein the therapeutic agent comprises the calcium channel blocker and the rho kinase inhibitor.

15. The method of claim 14, wherein the calcium channel blocker is nifedipine, and the rho kinase inhibitor is Y-27632.

16. The method of claim 13, wherein the ureter comprises a urinary stone lodged in the lumen of the ureter.

17. A method for relaxing human ureteral smooth muscle in vivo, the method comprising:
locally administering into a ureter of a patient, without aid of an infusion pump, a therapeutic agent to exhibit a relaxing effect on human ureteral smooth muscle of at least 20% when administered at a dose and concentration suitable for the locally administering,
wherein the therapeutic agent comprises an alpha-adrenergic receptor agonist, a phosphodiesterase type 5 inhibitor, or a combination thereof.

18. The method of claim 17, wherein the therapeutic agent comprises the alpha-adrenergic receptor agonist, and the alpha-adrenergic receptor agonist is tamsulosin.

19. The method of claim 17, wherein the ureter is exposed to the alpha-adrenergic receptor agonist at a concentration of about 0.5 µM to about 3.0 µM.

20. The method of claim 17, wherein the therapeutic agent comprises the phosphodiesterase type 5 inhibitor, and the phosphodiesterase type 5 inhibitor is vardenafil.

21. The method of claim 20, wherein the ureter is exposed to the phosphodiesterase type 5 inhibitor at a concentration of about 4 µM to about 8 µM.

22. The method of claim 1, wherein the formulation comprises a hydrogel having a viscosity that delays passage of the formulation from the ureter.

* * * * *